United States Patent [19]

Alaska

[11] Patent Number: 5,667,676
[45] Date of Patent: Sep. 16, 1997

[54] SIDE-PACKED CHROMATOGRAPHIC COLUMN

[76] Inventor: Andrew B. Alaska, 25330 SE. 36th Ct., Issaquah, Wash. 98029

[21] Appl. No.: 641,522

[22] Filed: May 1, 1996

[51] Int. Cl.$^6$ .................................................. B01D 15/08
[52] U.S. Cl. ........................ 210/198.2; 210/656; 96/105
[58] Field of Search ............................. 210/657, 656, 210/658, 659, 198.2; 96/101, 105, 107

[56] References Cited

U.S. PATENT DOCUMENTS

| | | | |
|---|---|---|---|
| 3,682,315 | 8/1972 | Haller | 210/233 |
| 3,780,866 | 12/1973 | Ek et al. | 210/198.2 |
| 4,497,711 | 2/1985 | Shepherd | 210/656 |
| 4,557,830 | 12/1985 | Onitsuka | 210/198.2 |
| 4,578,193 | 3/1986 | Shepherd | 210/656 |
| 4,604,198 | 8/1986 | Daily et al. | 210/198.2 |
| 4,676,898 | 6/1987 | Saxena | 210/198.2 |
| 4,710,289 | 12/1987 | Wermuth | 210/198.2 |
| 4,719,011 | 1/1988 | Shalon et al. | 210/198.2 |
| 4,722,786 | 2/1988 | Weaver | 210/198.2 |
| 4,892,654 | 1/1990 | Nickerson | 210/198.2 |
| 5,089,125 | 2/1992 | Hart et al. | 210/198.2 |
| 5,334,310 | 8/1994 | Frechet et al. | 210/198.2 |

*Primary Examiner*—Ernest G. Therkorn
*Attorney, Agent, or Firm*—Dean A. Craine

[57] ABSTRACT

The present invention describes a fixed volume, vertical flow chromatographic column. The column comprises a column member having an inner chamber for containing the particulate sorbent in a space surrounded by sidewalls and two flat frits, one on the top and one on the bottom. The sidewall has at least one dedicated packing port formed therein through which the sorbent may be packed into and unpacked from the column member. Upon the completion of the packing process, a plug is placed into the packing port flush with the inside surface of the sidewall. The frits are covered and supported by two lids. The lids have plumbing ports formed therein through which a liquid sample enters and exits the column member. The plumbing posts are horizontal disposed on opposite sides of the lids so that the flow of liquid sample is the same.

13 Claims, 7 Drawing Sheets

SIDE-PACKED CHROMATOGRAPHIC COLUMN

BACKGROUND OF THE INVENTION

1. Field of the Invention

This invention relates to liquid chromatography and, more particularly, to chromatographic columns which have one or more ports that enable packing of the sorbent material into the column's chamber.

2. Description of the Related Art

A chromatographic column has an inner chamber that contains a particulate sorbent surrounded by sidewalls and two screens. The screens prevent the sorbent from escaping the inner chamber yet allow the free flow of liquid sample therethrough. The screens typically are made of mesh or porous membrane, commonly referred to as a frit.

Chromatographic separation of the components from a liquid sample occurs on the sorbent. Fine and reproducible separation of a liquid sample is accomplished through even flow distribution across a uniformly packed sorbent. Dead spaces and voids in the column or sorbent causes uneven flow of the liquid sample through the sorbent which produces so-called "chromatographic peak tailing".

Besides its chromatographic performance, the quality of a column is also determined by its convenience in packing, unpacking, cleaning, consistency in performance from one packing to another, and convenience in handling and storage.

Historically, two types of columns are used: fixed volume, and adjustable volume.

Fixed volume columns usually comprise a cylindrical tube filled with a sorbent with two end plates disposed over the opened ends of the cylindrical tube. Fixed volume columns are useful because they provide consistent chromatographic conditions and allow for easy data comparison from different experiments and between different laboratories. Fixed volume columns are also less expensive than adjustable volume columns.

One major disadvantage of fixed volume columns is their cumbersome packing procedure which requires the use of an extension chamber installed over one end of the cylindrical tube in place of an end plate. After the cylindrical tube has been packed with sorbent, the extension chamber is then carefully removed and replaced with a frit and an end plate. Unfortunately, dead spaces or voids may be created in the column or sorbent when the extension chamber is replaced.

The problems associated with packing a fixed volume column have been addressed in U.S. Pat. Nos. 4,497,711 and 4,578,193 which disclose using a special valve that passes through an end plate and a porous bed-retaining membrane. Another method for packing the column is to create a sorbent slurry which is then feed through a narrow, filler tube attached to the sidewall of the column. Once the column is filled, additional sorbent is deposited inside the filler tube to form a seal that prevents the sorbent from escaping from the column.

Unfortunately, there are several disadvantages with columns that have filler tubes for packing sorbent. First, such columns are not reusable since the sorbent can not be removed from the column through the filler tube. Second, the sorbent may settle in the column over time thereby creating voids. Ideally, it would be desirable to pack additional sorbent into the column to fill these voids and to restore the column's performance. However, since the filler tube is sealed, packing additional sorbent into the column is precluded. Third, the filler tube creates a long and narrow dead space where a portion of the liquid sample can reside which can cause peak tailing in the chromatographic separation. The column is hard to validate for sterile applications since, when this occurs, microorganisms can survive cleaning agents in the stale solution of the long and narrow filler tube.

The second type of chromatographic column, called adjustable volume column, includes a plunger which is adjusted in height and positioned against the sorbent to tightly pack the sorbent inside the column. The main advantage of adjustable volume columns over fixed volume columns is that the sorbent may be quickly and neatly packed inside the column. One drawback with these columns, however, is that the volume of the sorbent is difficult to reproduce. Another drawback is that the plungers themselves can create sealing problems, especially when large diameter columns are used.

In addition to the two general types of chromatographic columns mentioned above, chromatographic columns can also be classified according to the direction of liquid sample flow in the column—horizontal flow and vertical flow. The packing process is relatively easy and reliable in horizontal flow column designs as disclosed in U.S. Pat. No. 4,676,898 (Saxena). In the column design disclosed therein, the end plate is equipped with two packing ports for packing. Unlike the vertical flow columns, the liquid sample in horizontal flow columns flows perpendicular to the column's longitudinal axis. The sorbent is contained in the column by top and bottom flat end plates and on the sides by two circular frits coaxially positioned with respect to each other.

Besides the packing and unpacking convenience, the column design should allow for the easy transfer of chromatographic conditions from small to large size columns, known as "scaling up". When "scaling up", it is desirable to keep the thickness of the sorbent constant so that the volume of the sorbent is increased only by increasing the cross-sectional area of the column. When this is done, the back pressure and sample elution times will remain constant throughout the "scaling up" process. The solvent and sample volumes are then directly proportional to the column size.

Vertical flow columns which have relatively high ratios of cross-section to height dimensions are known as "pancake shaped" columns. In these columns, the end plates or plungers have to be thicker than the column's sidewalls to withstand the pressure which builds up inside the column. This makes large "pancake shaped" columns heavy and expensive to construct and difficult to service.

The flow distribution of a liquid sample in a large "pancake shape" column also presents problems. As shown in FIGS. 1A–1C, when a liquid sample enters the column through an inlet port located in the center of the column, it spreads evenly over the frit. The portion of the liquid sample that flows through the center of the sorbent follows a shorter path and reaches the outlet port before the portion of the sample mixture that travels along the sidewall, through the sorbent, and then back to the center to the outlet port. As a result, the flow of the liquid sample through the column is uneven which causes tailing of the chromatographic peaks, as illustrated in FIG. 2. To correct this tailing problem, special flow adapters must be used in the column.

In an attempt to improve flow distribution of the liquid sample through the column, plumbing ports may be disposed horizontally in the column as suggested in U.S. Pat. No. 4,722,786. This design includes a bell-shaped end plate placed over the frit. No prototype is available on the market for this design for testing on either a small or large scale basis. It is anticipated that an extremely large dead space is created under the end plate which will ruin separation due to mixing of the sample components.

Another important feature of a chromatographic column is the convenience of handling and storage. Most of the columns currently available, have liquid sample inlet and outlet ports positioned vertically in the center of the column. The location of these ports on the column necessitates suspending the column from a stand to prevent pinching or crushing of the lower plumbing tube under the weight of the column. If the column could support its weight by standing on its end plate, the need for a heavy stand could be eliminated. However, the vertical disposition of the plumbing ports located in the center of the flat end plate makes self-supporting columns impossible.

In summary, all chromatographic columns in the prior art have certain undesirable features that distinguish them from the chromatographic column disclosed herein. These undesirable features include:

(1) all must be packed and unpacked either from the top or the bottom opening but not through their sidewalls except for those which use filler tubes;
(2) those having filler tubes are not reusable;
(3) the inlet and outlet ports are disposed vertically on the bottom end plate which prevents them from being used directly on a horizontal surface;
(4) all columns must use flow distributors which help distribute the liquid sample from a central located inlet port over the entire surface of the frit simultaneously to reduce peak tailing; and,
(5) all columns require that the flow direction through the column be reversed to remove an air bubble from the top frit which can ruin the chromatographic separation, especially if the gradient elution was in progress.

Chromatographic columns which do not have these undesirable features would be highly desirable.

SUMMARY OF THE INVENTION

One object of the present invention is to provide a chromatographic column where uniform, tight packing can be easily and repeatedly achieved in a short time and in reproducible volume.

Another object of the present invention is to provide a single chromatographic column design that can be "scaled-up" to different volumes, from 1 ml to hundreds of liters.

Another object of the present invention is to provide a chromatographic column design with minimal dead spaces and flow pathways having similar lengths to minimizes tailing of a sample peak.

A further object of the present invention is to provide a chromatographic column design that does not require a sophisticated stand so that a column can be placed on a bench or floor without fear of breaking or pinching the tubing at the bottom.

A still further object of the present invention is to provide a column design where an air bubble or precipitate or other unwanted materials could be easily removed directly from the surface of the frit without reversing the liquid flow through the column.

The above objects are accomplished by providing the vertical flow chromatographic column disclosed herein which includes a cylindrical or polygonal-shaped column member with at least one side-packing port integrally formed on the sidewalls thereof which enables particulate sorbent to be easily packed or unpacked from the column member. The packing port, or ports, are made sufficiently wide and short to prevent sorbent from self-sealing and to allow for quick and easy packing and unpacking of the sorbent from the column member. Upon completion of the packing process, a removable plug is inserted into the packing port with it's inside surface positioned flush with the inside surface of the column member thereby eliminating any dead space. The removable plug also prevents discharge of the sorbent or the liquid sample through the packing port during use. In one embodiment, the cross-section of the column member wall is rectangular so that the removable plug can be easily positioned flush with the column member's sidewall.

The column member itself has top and the bottom openings over which a frit and a lid are disposed. The inlet and outlet plumbing ports are manufactured on opposite sides of the upper and lower lids to ensure that any flow path of the liquid sample through the column has similar length, thereby eliminated the need for sophisticated flow distributors.

In one embodiment, inlet and outlet plumbing ports are longitudinally aligned on the vertical sides of the upper and lower lids perpendicular to the column member's longitudinal axis. This feature prevents accidental damage to the plumbing ports and tubing under the weight of the column, and eliminates the need for a column stand.

In yet another embodiment, each lid is equipped with at least two plumbing ports disposed on opposite sides thereof. This feature allows for removal of air bubbles, precipitate, or other unwanted materials directly from the surface of the frit through the plumbing ports without reversal of the flow of the liquid sample.

DESCRIPTION OF THE PREFERRED EMBODIMENT(S)

Figure 1:
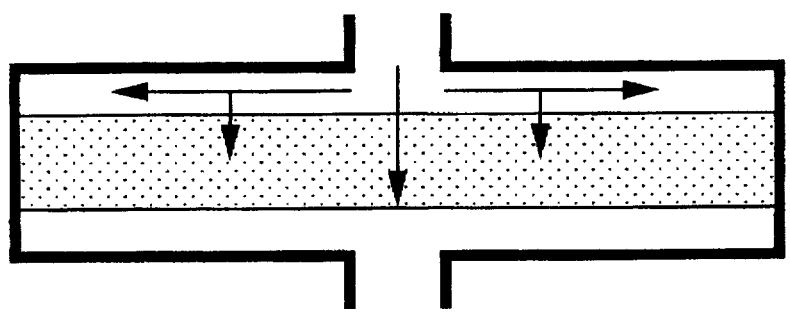
FIGS. 1A–1C illustrate how a liquid sample progressively flows through a conventional vertical flow chromatographic column.
Figure 1:
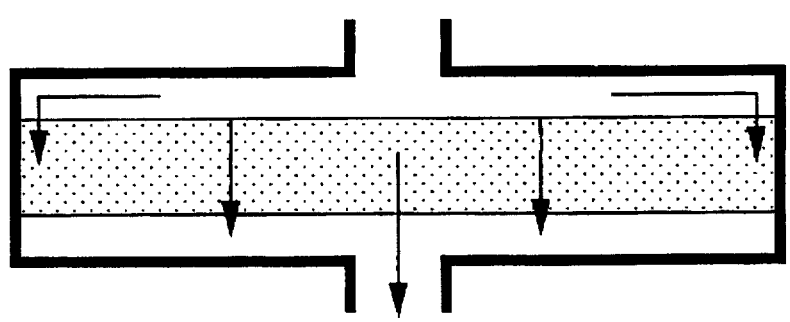
Figure 1:
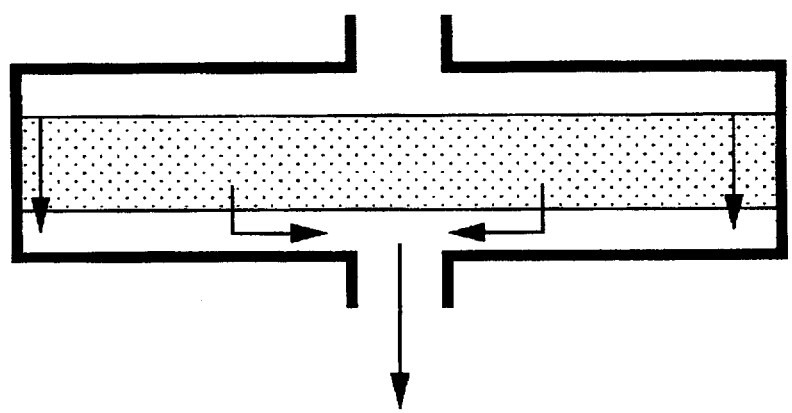
Figure 2:
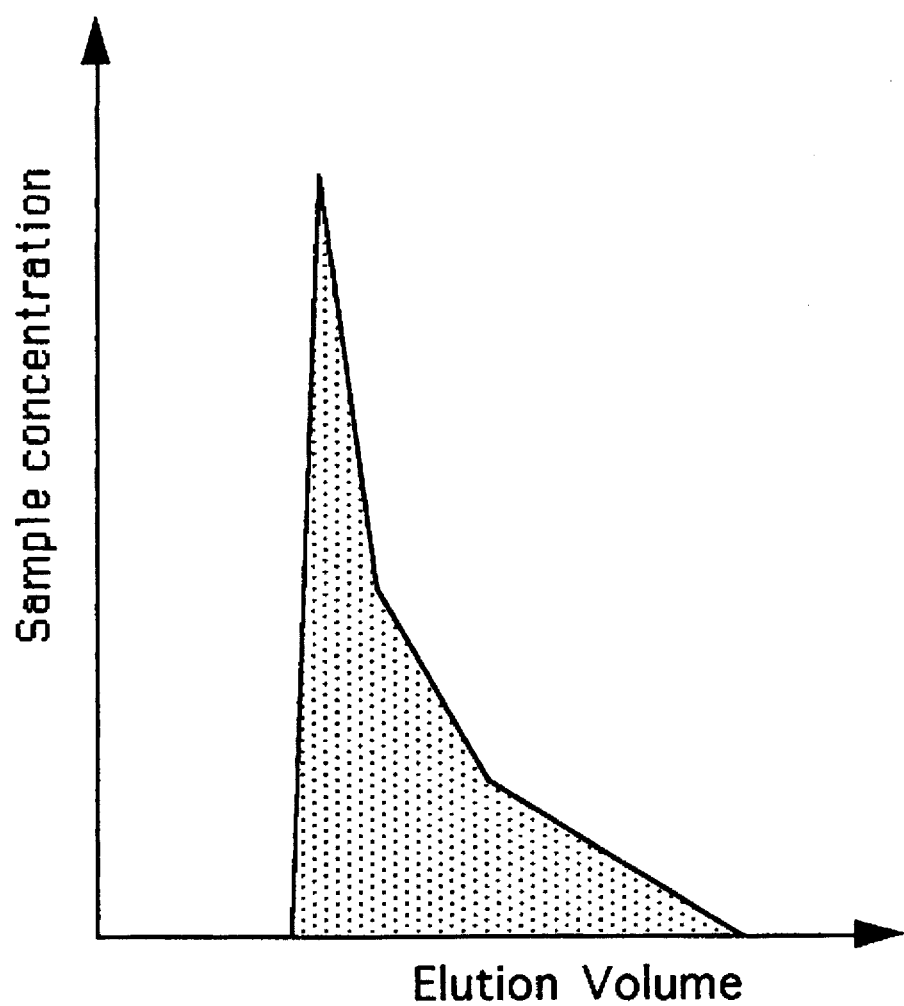
FIG. 2 is a graph showing the elution profile of a liquid sample from a conventional vertical flow chromatographic column.
Figure 3:
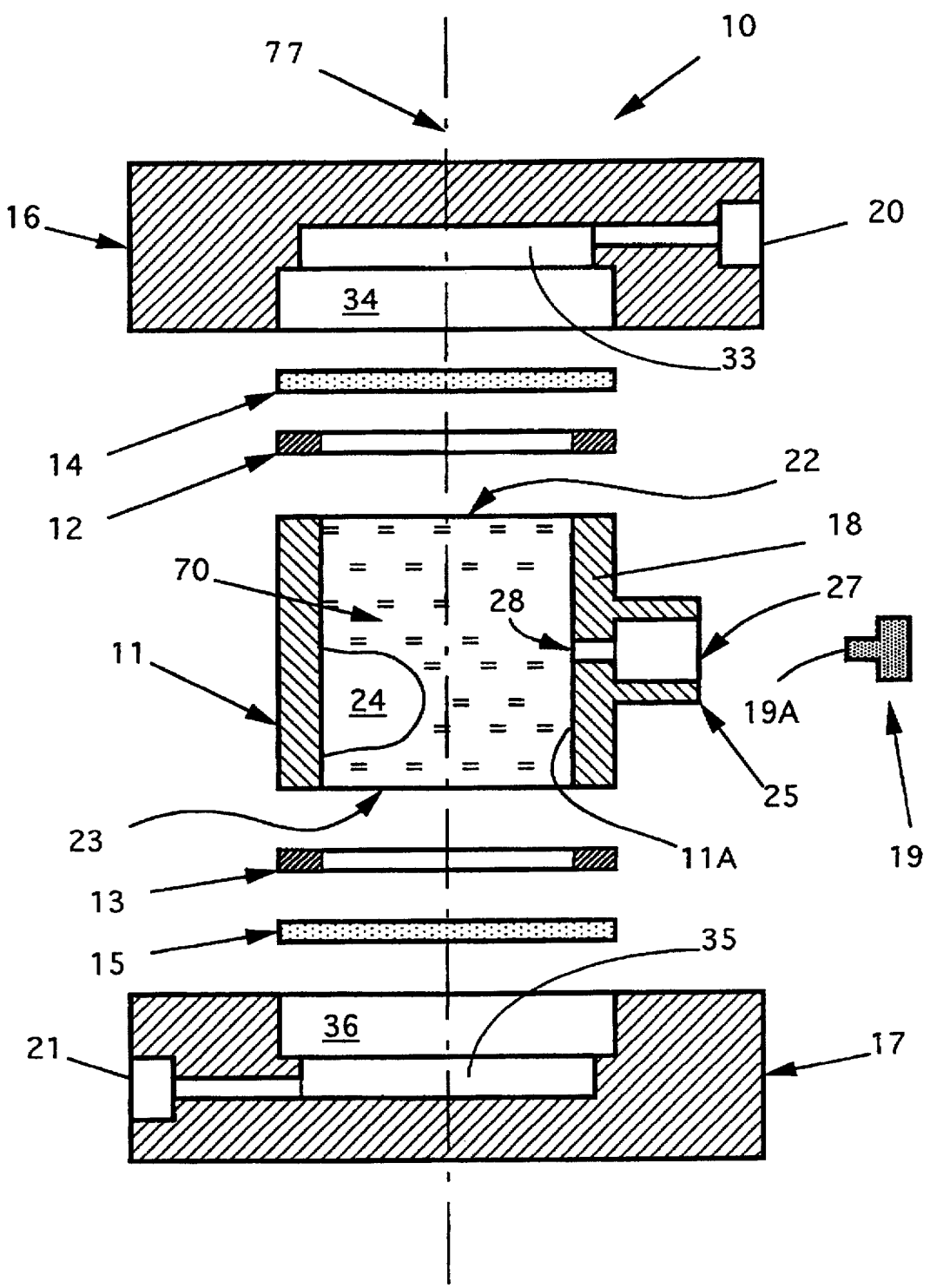
FIG. 3 is an exploded, cross-sectional view of one embodiment of the side-packed chromatographic column in accordance with the invention.

FIG. 3 is an exploded, cross-sectional view of one embodiment of the side-packed chromatographic column, referred generally as 10. The column 10 comprises a column member 11 with top and bottom openings 22, 23, respectively. Disposed over the top and bottom openings 22, 23 is an upper sealing member 12 and a lower sealing member 13, respectively. Disposed over each upper and lower sealing member 12, 13 is an upper frit 14 and a lower frit 15, respectively. An upper lid 16 and a lower lid 17 are then disposed over each upper frit 14, upper sealing member 12, and lower frit 15, lower sealing member 13, respectively, and attaches to the column member 11. When completely assembled, a closed chamber 24 is formed inside the column member 11 in which sorbent 70 is packed.

Integrally formed on the sidewall 18 of the column member 11 is a laterally extending packing port 25. During the packing procedure, sorbent 70 is inserted and packed into the closed chamber 24 through the packing port 25. The packing port 25 has an outer opening 27 and an inner opening 28. The inner opening 28 communicates with the closed chamber 24 and has a sufficient diameter so that the sorbent 70 can be easily packed and unpacked from the column member 11 during use. A removable plug 19 is placed into the packing port 25 to completely close and seal the chamber 24. The plug 19 is complementary in shape and size to the packing port 25 so that the plug's inside surface 19A is positioned flush with the inside surface 11A of the column member 11.

As mentioned above, the upper and lower lids 16, 17, respectively, are designed to fit over the top and bottom openings 22, 23, respectively, on the column member 11. In the embodiment shown in FIG. 3, the upper lid 16 has at least one inlet plumbing port 20 formed on its vertical surface thereon while the lower lid 17 has at least one outlet plumbing port 21 formed on its vertical surface. When the upper and lower lids 16, 17 are attached to the column member 11, the inlet and outlet plumbing ports 20, 21, respectively, are positioned on opposite sides of the column member's longitudinal axis 77. The inlet and outlet plumbing ports 20, 21, respectively, each communicate with a centrally located, small recessed area 33, 35, respectively, formed inside the upper and lower lids 16, 17, respectively. A large centrally located recessed area 34, 36 is formed adjacent to each small recessed areas 33, 35, respectively, which are designed to receive the upper and lower extending edges of the column member 11, the frits 14, 15, and the sealing members 12, 13, respectively, when the upper and lower lids 16, 17 are connected to the column member 11.

Figure 4:
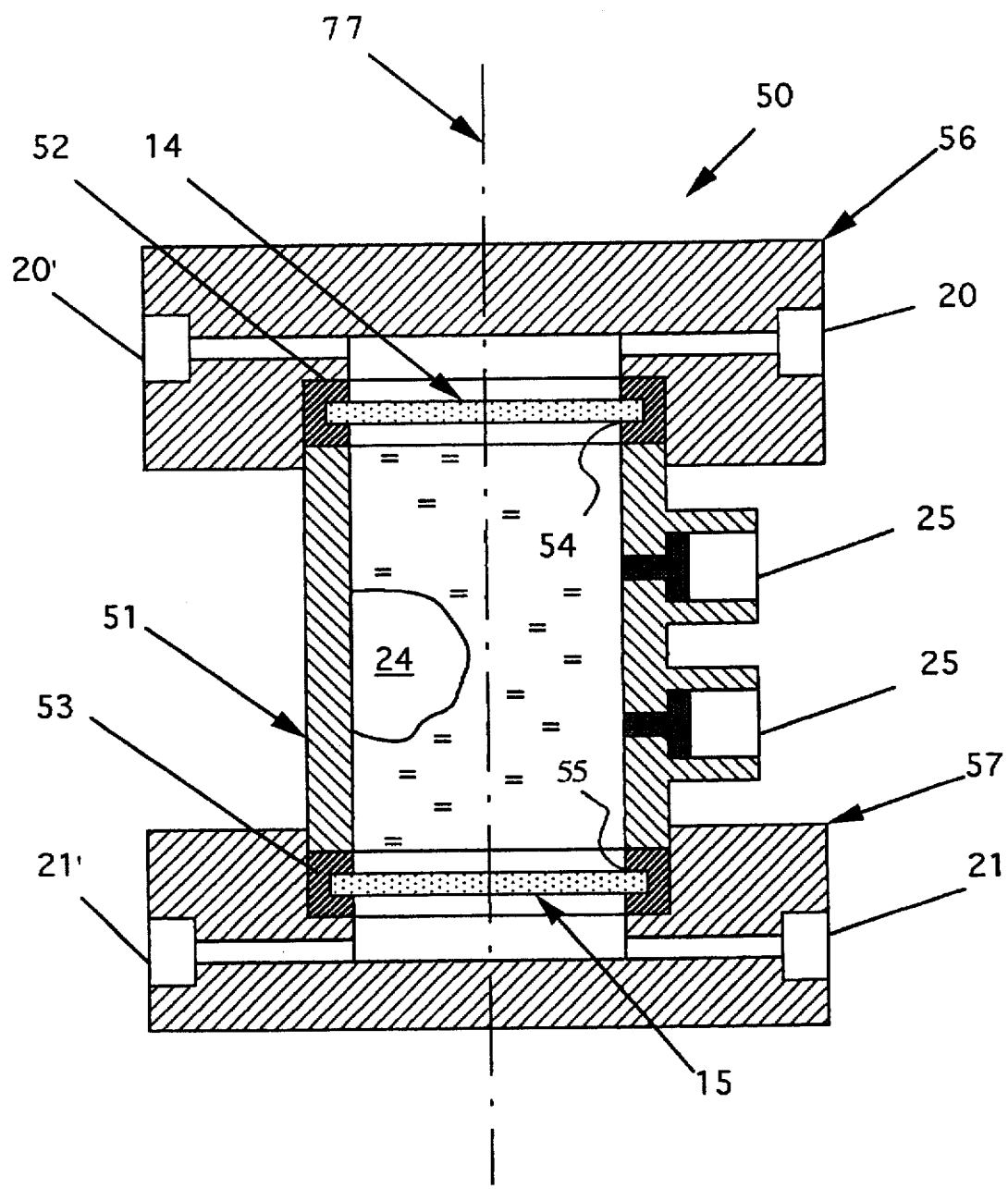
FIG. 4 is a cross-sectional view of a second embodiment of the side-packed chromatographic column with two packing ports formed in the sidewall of the column member and two plumbing ports formed in each upper and lower lid.

In FIG. 4, a second embodiment of the column, generally referred to as 50, is shown with a column member 51 having two, laterally extending side packing ports 25 formed therein to facilitate the packing of sorbent 70 into the column member 51. Column member 51 also has two upper and lower lids 56, 57, respectively, attached thereto. The upper lid 56 has two inlet plumbing ports 20, 20' formed on opposite sides thereof while the lower lid 57 has two outlet plumbing ports 21, 21' formed on opposite sides thereof. By providing two inlet and two outlet plumbing ports on opposite sides of the lids 56, 57 in this manner, air bubbles or particulate or other unwanted materials may be removed directly from the surface of the adjacent frit 14, 15.

The column members 11, 51 shown in FIGS. 3 and 4, respectively, can be either circular or polygonal in horizontal cross-section.

Figure 5:
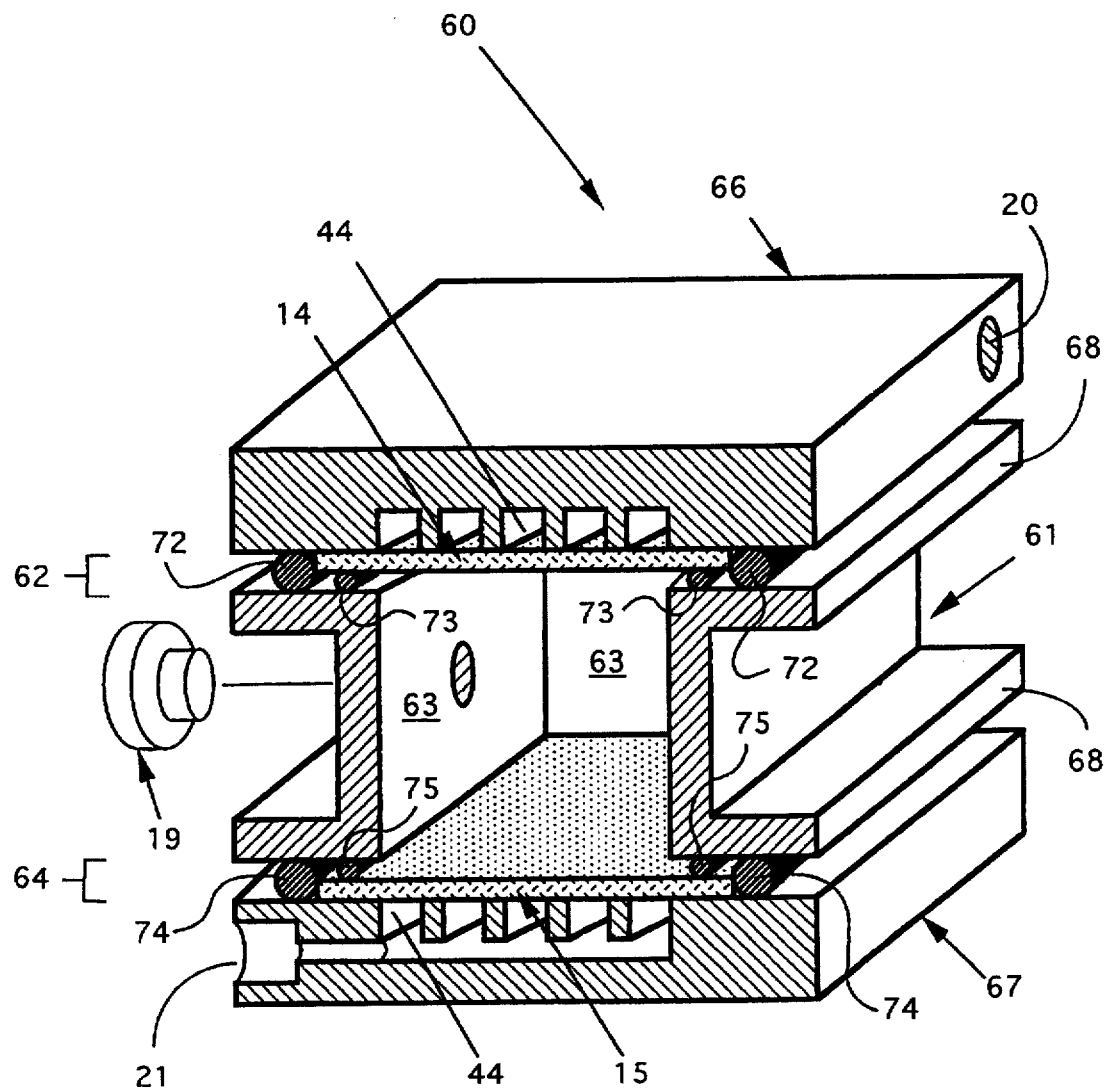
FIG. 5 is a cross-sectional view of a third embodiment of the side-packed chromatographic column having a polygonal-shaped column member.

In FIG. 5, a third embodiment of the side-packed chromatographic column, referred generally as 60, is shown having a column member 61 rectangular in horizontal cross-section. The column member 61 has four vertically aligned flat sidewalls 63 (three shown). Each sidewall 63 has an upper and lower flange surfaces 68. During assembly, the upper and lower sealing members 62, 64, respectively, are disposed against the flange surfaces 68. The upper and lower frits 14, 15 are disposed over the sealing members 62, 64, respectively. The upper and lower lids 66, 67 are then disposed over the upper and lower frits 14, 15. By providing flat sidewalls 63 on the column member 61, the plug 19 may be installed flush with the inside surface of the column member 61.

In column 60, transversely aligned grooves 44 are formed on the inside surfaces of the upper and lower lids 66, 67 which replace the small and large recessed areas 33, 34, and 36, 35, respectively, used on columns 10 and 50. The grooves 44 enable the liquid sample to flow from the inlet plumbing port 20 to any part of the frit 14. Grooves 44 can be replaced with any conventional means used to create a space between the frit and the adjacent lid. A distribution screen (not shown) may also be disposed between the frits and the adjacent lids.

Figure 6:
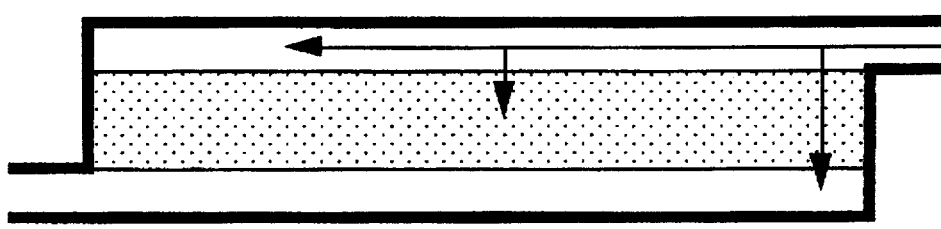
FIGS. 6A–6C illustrate how a liquid sample progressively flows through the chromatographic column in accordance with the invention.
Figure 6:
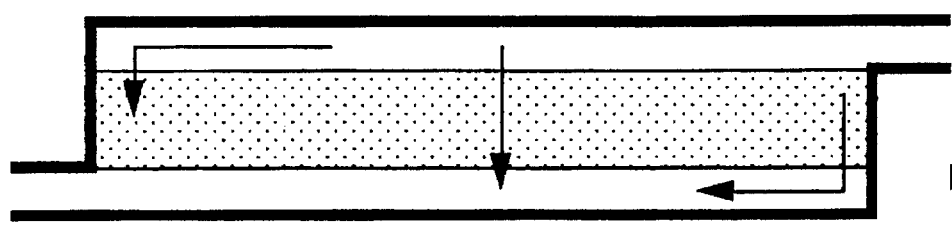
Figure 6:
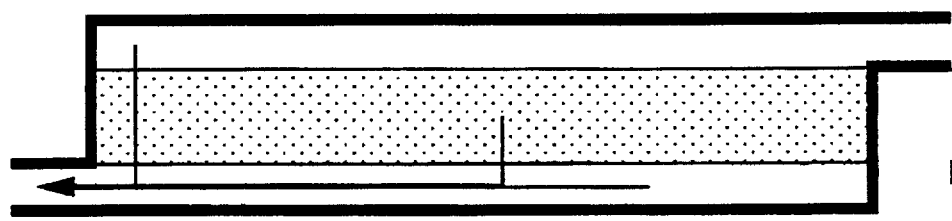
Figure 7:
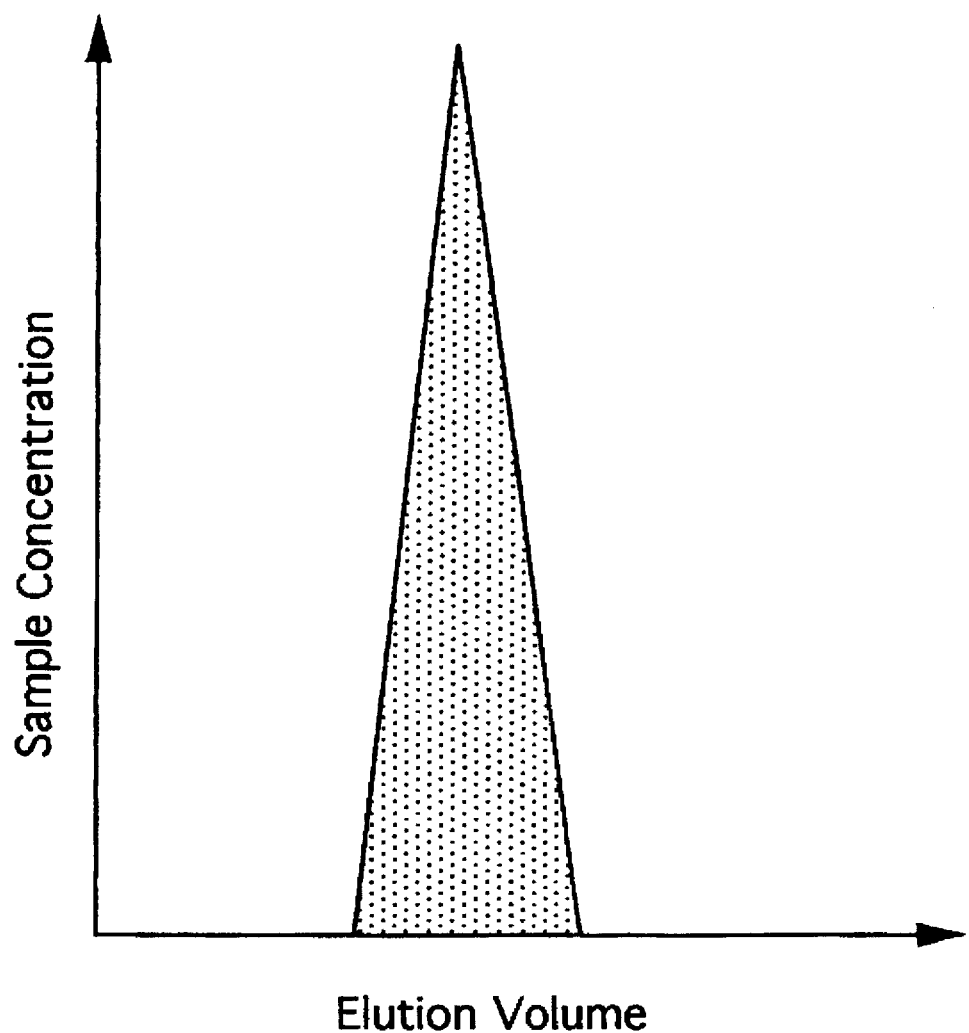
FIG. 7 is a graph showing the elution profile of the liquid sample from the chromatographic column in accordance with the invention.

Columns 10, 50, 60 all provide for an even flow of the liquid sample, as shown on FIGS. 6A–6C. During operation, the liquid sample is forced through the column member via the inlet pumping port and enters the small recessed spaced formed in the upper lid. The liquid sample then leaves the small recessed space and spreads evenly across the upper frit. The liquid sample then flows through the upper frit and through the sorbent to the lower frit. When the liquid sample flows through the lower frit, its drains into the outlet plumbing port located in the lower lid and on the opposite side of the column member. In this manner, the length of the liquid sample's flow through the column member is equal which reduces peak tailing, as shown on FIG. 7.

Columns 10, 50 and 60 may be assembled in any of the several ways conventionally employed in chromatography columns to provide a leak proof arrangement. For example, braces and/or bolts may be used to connect the two upper and lower lids to the column member. The circular cross-sectional shape of column 10 may allow lids 16, 17 to be screwed tightly to the column member 11 for which the lids 16, 17 and the column member 11 should have matching threads. It should also be understood that one lid and the column member 11 may combined to form a single member.

The sealing members serve two purposes. First, they ensure that the sorbent does not pass around the frit and into the plumbing port. Second, they prevent the liquid sample from escaping the column member between the upper and lower lids. The sealing members may be single structures as shown in FIGS. 3 and 4, and referred to as 12, 13 and 52, 53, respectively. The sealing members 12, 13 are disposed between the frits 14, 15, respectively, and the upper and lower edges of the column member 11. The sealing members 52, 53, have a central channel 54, 55 formed therein which receives the outer edge of the frits 14, 15, respectively. In FIG. 5, an alternatively sealing members are shown, referred to as 62 64, which include a pair of outer and inner gasket members 72, 73, and 74, 75, respectively. Each pair of outer and inner gasket 72, 73 and 74, 75, may be connected together or single elements. It should also be understood that the sealing members may be any cross-sectional known in the art to provide a leak proof seal.

The column members 11, 51, 61 and the upper and lower lids pair of lids 16, 17, and 56, 57, and 66, 67, may be constructed of stainless steel, aluminum or other metals and alloys, glass, ceramic, polymers and composite materials normally employed in chromatography to withstand solvent, pressure and temperature conditions. Similarly, the frits 14, 15 may be porous, sintered matter, or mesh material made of polypropylene, stainless steel, felt, or other porous material. The sealing members 12 and 13, 52 and 53, and 62 and 64, and the plug 19 may be constructed from rubber, polyethylene, Teflon™ and other materials used commonly in O-rings and other gaskets. The plug 19 may also comprise a LUER LOCK™ or a valve. Methods of manufacturing the above column elements include molding, gluing, welding and other techniques known in the art and chosen in accordance with properties of the material used.

In compliance with the statute, the invention described herein, has been described in language more or less specific as to structural features. It should be understood, however, the invention is not limited to the specific features shown, since the means and construction shown comprises only the preferred embodiments for putting the invention into effect. The invention is, therefore, claimed in any of its forms or modifications within the legitimate and valid scope of the amended claims, appropriately interpreted in accordance with the doctrine of equivalents.

I claim:

1. A vertical flow chromatography column comprising:
  a. a column member having top and bottom openings and a longitudinal axis;
  b. a pair of frits located over said top and bottom openings of said column member;
  c. at least one packing port manufactured on said column member enabling sorbent to be packed and unpacked from said column member;
  d. a removable plug attachable to said packing port capable of opening or closing said packing port;
  e. a pair of upper and lower lids attached over said top and bottom openings of said column member and over said frits disposed thereon, said upper and lower lids capable of evenly distributing a liquid sample placed thereon;
  f. at least one sealing member disposed between said upper and lower lids and said column member for sealing said top and bottom openings of said column member;
  g. at least one inlet plumbing port located on said upper lid to enable a liquid sample to be placed inside said column member; and,
  h. at least one outlet plumbing port located on said lower lid to remove a liquid sample from said column member, said outlet plumbing port being disposed on said lower lid so that said inlet plumbing port and said outlet plumbing port are on opposite sides of said longitudinal axis of said column member when said lids are attached to said column member.

2. The apparatus of claim 1, wherein said column member has a polygonal cross-section.

3. The apparatus of claim 2, wherein said column member has a rectangular cross-section.

4. The apparatus of claim 1, wherein said column member is circular in cross-section.

5. The apparatus of claim 1, wherein said upper lid has two inlet plumbing ports.

6. The apparatus of claim 1, wherein said lower lid has two outlet plumbing ports.

7. A chromatographic column utilizing vertical flow of the liquid sample through the packed sorbent, comprising:
  a. a vertical flow column, said column having surrounding side walls to create a longitudinally defined chamber inside said column, said column having a top and bottom opening and a longitudinal axis;
  b. at least one packing port manufactured in said column to enable sorbent to be packed into and unpacked from said chamber;
  c. a pair of frits located over said top and bottom openings of said column;
  d. upper and lower lids attached over said top and bottom openings of said column, said upper and lower lids each capable of evenly distributing liquid sample placed into said column across said frits;
  e. at least one plumbing port formed on each said upper and lower lid enabling a liquid sample to enter and exit said column during use; said plumbing ports being formed on said upper and lower lids so that when said upper and lower lids are attached to said column, said plumbing ports are disposed on the opposite sides of said column; and,
  f. a sealing member disposed between said column and each said upper and lower lid.

8. The apparatus in claim 7, further including a removable plug capable of being inserted into each said packing port to seal said column member.

9. The apparatus in claim 8 wherein said sidewall is rectangular in horizontal cross-section.

10. The apparatus in claim 8, wherein said sidewall is circular in horizontal cross-section.

11. The apparatus in claim 8, wherein said sidewall is polygonal in horizontal cross-section.

12. The apparatus in claim 7, wherein each said upper and lower lid has two plumbing ports formed therein to enable a liquid sample to enter and exit said columns.

13. The apparatus in claim 7, wherein said plumbing ports are disposed perpendicular to said longitudinal axis.

* * * * *